United States Patent
Hashimoto et al.

(10) Patent No.: US 9,302,271 B2
(45) Date of Patent: Apr. 5, 2016

(54) ION MOBILITY SEPARATION DEVICE

(75) Inventors: Yuichiro Hashimoto, Tokyo (JP); Hideki Hasegawa, Tokyo (JP); Masao Suga, Tokyo (JP); Hiroyuki Satake, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/411,217

(22) PCT Filed: Jul. 4, 2012

(86) PCT No.: PCT/JP2012/067060
§ 371 (c)(1),
(2), (4) Date: Dec. 24, 2014

(87) PCT Pub. No.: WO2014/006698
PCT Pub. Date: Jan. 9, 2014

(65) Prior Publication Data
US 2015/0190815 A1  Jul. 9, 2015

(51) Int. Cl.
| | |
|---|---|
| H01J 49/02 | (2006.01) |
| B03C 7/02 | (2006.01) |
| G01N 27/62 | (2006.01) |
| G01N 27/447 | (2006.01) |
| B03C 3/017 | (2006.01) |
| B03C 3/08 | (2006.01) |
| B03C 3/12 | (2006.01) |
| B03C 3/41 | (2006.01) |
| B03C 3/47 | (2006.01) |
| B03C 3/68 | (2006.01) |

(52) U.S. Cl.
CPC . *B03C 7/02* (2013.01); *B03C 3/017* (2013.01); *B03C 3/08* (2013.01); *B03C 3/12* (2013.01); *B03C 3/41* (2013.01); *B03C 3/47* (2013.01); *B03C 3/68* (2013.01); *G01N 27/447* (2013.01); *G01N 27/624* (2013.01)

(58) Field of Classification Search
None
See application file for complete search history.

(56) References Cited

U.S. PATENT DOCUMENTS

| | | | |
|---|---|---|---|
| 5,180,480 A | 1/1993 | Manz | |
| 6,495,823 B1 | 12/2002 | Miller et al. | |
| 6,512,224 B1 | 1/2003 | Miller et al. | |
| 2001/0023825 A1* | 9/2001 | Frumin | G01N 27/44773 204/458 |
| 2010/0148053 A1 | 6/2010 | Belford et al. | |

FOREIGN PATENT DOCUMENTS

| | | |
|---|---|---|
| JP | 5-80032 A | 3/1993 |
| JP | 2003-514349 A | 4/2003 |
| JP | 2012-512506 A | 5/2012 |

OTHER PUBLICATIONS

International Search Report dated Jul. 31, 2012 with English translation (five (5) pages).

* cited by examiner

*Primary Examiner* — Arun S Phasge
(74) *Attorney, Agent, or Firm* — Crowell & Moring LLP (57) ABSTRACT

In an ion mobility separation device, there are problems that while arraying of separation electrodes and flow paths is restricted, time required for scanning correction voltages becomes longer and the throughput is reduced when the correction voltages are set in detail. These problems are solved for example by the following means. Namely, an ion mobility separation device characterized in that: at least one of a pair of plate electrodes has a first electrode section having a first conductivity, a second electrode section having a second conductivity, and a third electrode section interposed between the first electrode section and the second electrode section, wherein the third electrode section has a third conductivity smaller than the first conductivity and the second conductivity; the first electrode section, the second electrode section and the third electrode section are aligned in a direction perpendicular to a flow path; and a voltage controller applies different direct-current voltages to the first electrode section and the second electrode section.

6 Claims, 6 Drawing Sheets

ION MOBILITY SEPARATION DEVICE

TECHNICAL FIELD

The present invention relates to an ion mobility separation device.

BACKGROUND ART

Ion mobility separation devices, which separate and detections according to their ion mobilities, are widely used as devices for on-site measurement such as environmental analysis, detection of explosives, detection of illegal drugs and detection of chemicals, owing to their capability to operate at atmospheric pressure without requiring a vacuum pump. In ion mobility separation devices, a technique for separating ions generated by an ion source with high accuracy and then detecting the ions with high sensitivity and high throughput is considered to be important in order to further broaden their applications and reduce the false detection.

PTL 1 describes a method for reducing the size of an ion mobility separation device and increasing its throughput using plate insulator materials such as glass. PTL 1 also describes a method in which current detection electrodes are disposed in the direction in which ions travel to increase the ability by using plate insulator materials.

CITATION LIST

Patent Literature

PTL 1: U.S. Pat. No. 6,495,823

SUMMARY OF INVENTION

Technical Problem

In an ion mobility detector, which separates and detects ions according to their ion mobilities, a technique for separating and detecting ions generated by an ion source with high sensitivity, high accuracy and high throughput is important. In particular, in a field asymmetric ion mobility detector, increase of the ion resolution and increase of the throughput have been conflicting factors. That is, when the correction electric field is set in detail to increase the ion resolution, the time required for scanning the measurement condition becomes longer and this causes the reduction of the throughput.

Although PTL 1 discloses that the throughput is increased by arraying separation electrodes and flow paths, arrayed separation electrodes cause the charge-up phenomenon in insulator parts in the gaps of the arrayed electrodes or generate a fringing field, resulting in a problem of deteriorated resolution or specificity. This problem arises remarkably, especially when the array distances become finer. In addition, arrayed flow paths also cause a problem of deteriorated resolution or specificity due to the flow generated by the friction against the wall surfaces.

Solution to Problem

The above problems are solved for example by the following means. Namely, an ion mobility separation device: which comprises an ion source generating ions; a pair of spaced plate electrodes defining a flow path between a sample inlet and a sample outlet of the ions; a voltage controller for applying an asymmetric time-varying voltage and direct-current voltages to the plate electrodes; and current detectors aligned in a direction perpendicular to a flow-path direction and a direction in which the asymmetric time-varying voltage is applied: wherein at least one of the pair of plate electrodes contains a first electrode section having a first conductivity, a second electrode section having a second conductivity, and a third electrode section interposed between the first electrode section and the second electrode section, wherein the third electrode section has a third conductivity smaller than the first conductivity and the second conductivity; the first electrode section, the third electrode section and the second electrode section are aligned in a direction perpendicular to the flow-path direction and the direction in which the asymmetric time-varying voltage is applied; and the voltage controller applies different direct-current voltages to the first electrode section and the second electrode section.

Advantageous Effects of Invention

According to the invention, it becomes possible in a field asymmetric ion mobility separation device to obtain spectra corresponding to correction voltages simultaneously, while the deterioration of the resolution due to the charge-up phenomenon is reduced, and thus the throughput and the resolution can be compatible.

DESCRIPTION OF EMBODIMENTS

Example 1

Figure 1:
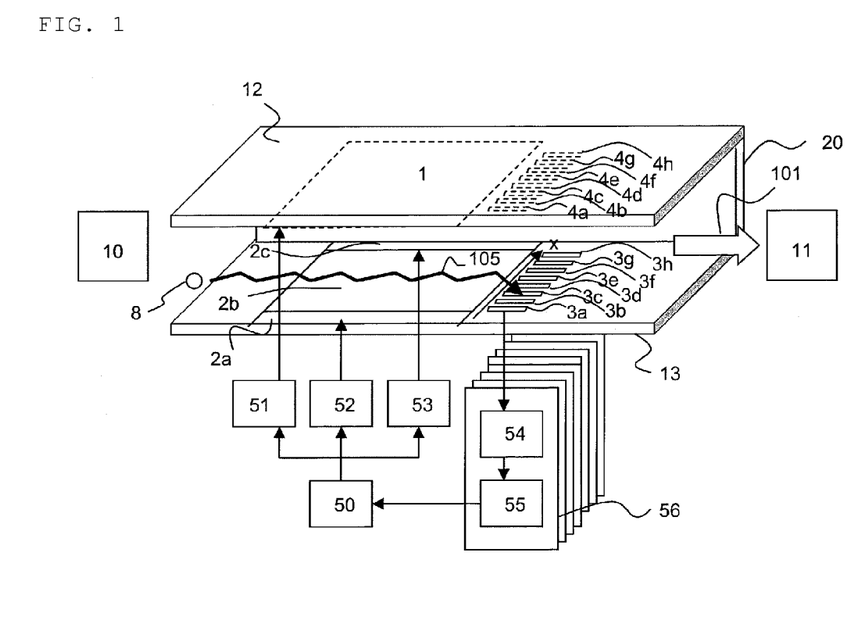
FIG. 1 A diagram showing an example of the constitution of the invention.

FIG. 1 is a constitution diagram of an ion mobility separation device to which this system is applied. An ion 8 generated by an atmospheric-pressure ion source 10, for example an atmospheric-pressure chemical ion source, an atmospheric-pressure photoexcitation ion source, an electrospray ion source or a dielectric barrier discharge ion source, is introduced to a space surrounded by a substrate 12, a substrate 13 and spacers 20 (the spacer in front is not shown in the diagram) by a gas flow 101 generated by a pump 11 containing a diaphragm pump or the like. When the substrate 12 and the substrate 13 are constituted by an insulator such as glass, plastic and ceramic, the production is easier, in view of necessity of disposing various electrodes on the surfaces thereof. In addition, a distance d between the substrate 12 and the substrate 13 is generally set at about 50 µm or more and 2 mm or less. As the distance d becomes larger, there is a disadvantage that higher voltage values are required for the separation voltage and the correction voltages described below. On the other hand, as the distance d becomes smaller, there is a disadvantage that the ion transmittance deteriorates due to the disturbed flow near the wall surfaces, the diffusion of the ions, the ion motion between the separation electrodes due to the separation voltage and the like. The ion 8 travels in a traveling direction 105 by a resultant force of a force received from the gas flow 101 and the asymmetric electric field and the correction electric field generated between separation electrodes 1 and 2 by power sources 51, 52 and 53. Transit time t through the separation electrodes 1 and 2 is about several ms or more and several hundred ms or less and the transit time is determined by equation: t=F/dwl, where F is the gas flow in the pump, d is the distance between the separation electrodes, w is the width of the separation electrodes and l is the length of the separation electrodes in the traveling direction. As the transit time becomes shorter, there is an advantage that the transmittance becomes higher: while as the transit time becomes longer, there is an advantage that higher resolution can be achieved. An ion which has passed through the separation electrodes reaches a cation detection electrode 3 when it is a cation or an anion detection electrode 4 when it is an anion. In order that ions can reach the detection electrodes efficiently, a direct-current voltage of several V or more and several dozen V or less is applied to the cation detection electrode 3 and the anion detection electrode 4. An ion which has reached the detection electrode is sent to a signal processor 56, amplified by a weak-current amplifier 54 and then recorded in a recorder 55 as a signal. Although it is not shown in FIG. 1, ions which do not pass through the electrodes reach the substrate 12 or the substrate 13 and lose their charges and hence these ions are not detected as signals. Furthermore, although only the signal processors for cations are shown in FIG. 1, the signal processing of anions after reaching the anion detection electrode 4 is the same.

Figure 2:
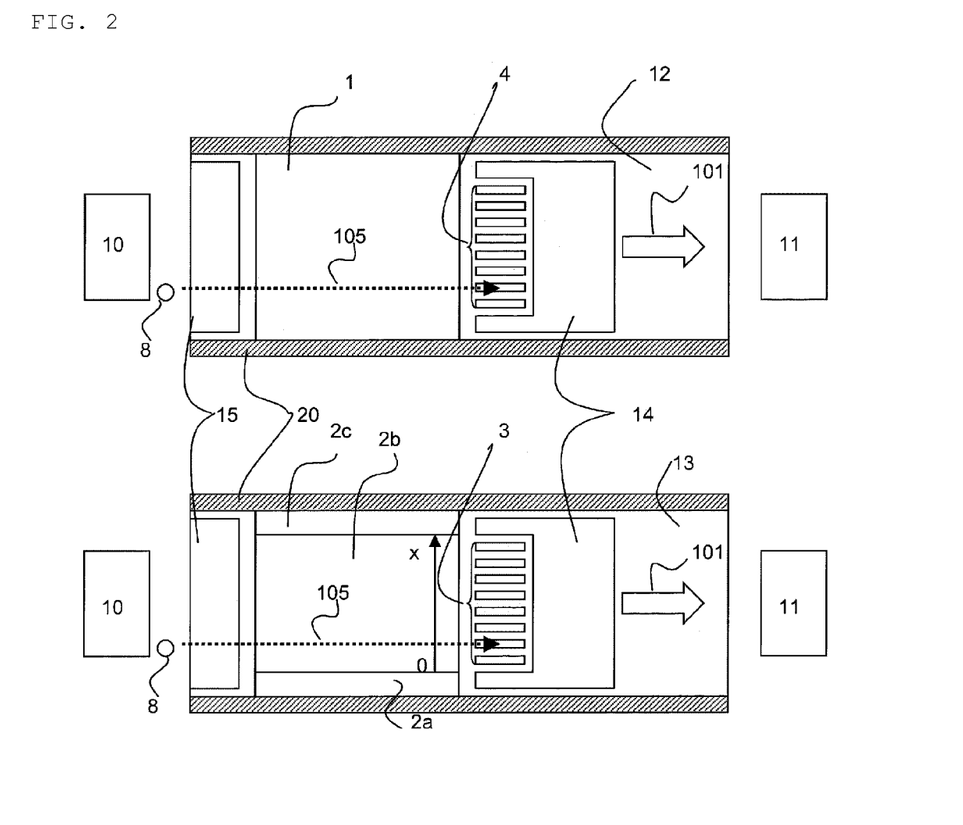
FIG. 2 A supplementary diagram showing an example of the constitution of the invention.

Example 1 is supplementarily explained using FIG. 2. FIG. 2 shows two-dimensional sections on the substrate 12 and the substrate 13 where FIG. 1 is cut through a plane parallel to the substrate 12. The ion 8 travels along the gas flow 101 in the ion-traveling direction 105.

Because the flow of the gas is disturbed near the spacers 20, it is desirable to use areas other than the areas near the spacers 20 (around 2d) for the ion separation sections. In this case, it is possible to make a modification in which the separation electrode(s) is(are) divided into sections with high conductivities (2a and 2c) and a section with a low conductivity (2b) and thus the value of the voltage applied to this section (2b) is controlled low. The sections with high conductivities (2a and 2c) are metals or the like: while the section with a low conductivity (2b) has semiconductivity and can be produced from for example a metal oxide thin film, a metal nitride thin film or an organic conductor. When the widths of the sections 2a, 2b and 2c are all 1 cm for example, the power consumption becomes about one third by producing only the section 2b from a substance with a low conductivity and the risk of the damage of a separation electrode 2 due to the temperature rise can be reduced. The section with a low conductivity (2b) has an end-to-end resistance of about 50 Ω or more and 5 kΩ or less. As the end-to-end resistance becomes larger, there is a disadvantage that the influence of the surrounding electrical noise becomes greater or the separation voltage distorts at around the center: while when the end-to-end resistance is decreased, the power consumption increases and there is a risk of the damage of the separation electrode 2 due to the temperature rise. However, an end-to-end resistance in the above range can solve both problems. It is possible to make a modification in which the value of the voltage applied to 2b is controlled low, also by reducing the numbers of the detection electrodes and the signal processors thorough disposing the detection electrodes 3 and 4 on areas except for the areas near the spacers. On the other hand, when different DC voltages are applied to electrodes sectioned as in PTL 1, there is a problem that the charge-up phenomenon or the like is caused in the insulator parts between the electrodes and the electric field is disturbed, resulting in the deterioration of the resolution.

Figure 3:
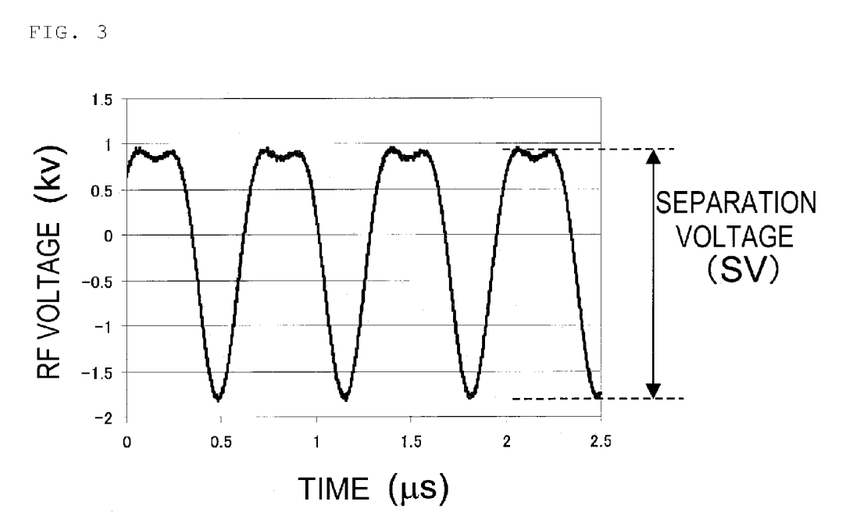
FIG. 3 A diagram showing an example of the separation voltage of the invention.

A composite voltage of a separation voltage (SV), which is an asymmetric voltage, and a calibration voltage (CV) is applied to the separation electrode 1 and the separation electrode 2 by the power sources 51, 52 and 53. An example of the separation voltage to be applied is shown in FIG. 3. This composite wave is represented by (Math. 1) and shows an example of the sum of sine waves with frequencies f of 1.5 MHz and 3 MHz. Here, $V_{main}$ is the amplitude of the component with a low frequency (1.5 MHz here) and $V_{sub}$ is the amplitude of the component with a high frequency (3.0 MHz here). By setting $V_{sub}/V_{main}$ to about ⅕ to ½, a waveform imitating a square wave can be created. The phase difference is adjusted in such a way that the ratio of the square wave becomes high.

$$\text{Composite Wave} = V_{main} \sin(2\pi f t) + V_{sub} \cos(2\pi (2f) t + \phi) \quad \text{(Math. 1)}$$

In addition to the above example, the separation voltage (SV), which is an asymmetric voltage, varies widely for example a square wave. By using a wave with a high frequency and a harmonic wave thereof as described above, it is possible to generate an asymmetric voltage of several kV relatively easily with a single coil.

The calibration voltage varies depending on the position in the x-direction (see FIG. 2) and is represented by (Math. 2) where Va and Vc are the voltages applied to 2a and 2c, respectively, and s is the width of the section 2b with a low conductivity.

$$CV(x) = Va + (Vc - Va)x/s \quad \text{(Math. 2)}$$

Figure 4:
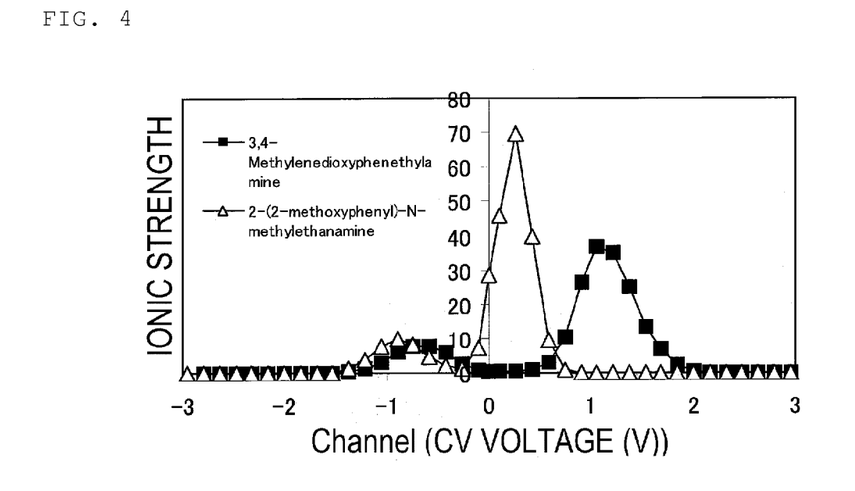
FIG. 4 A diagram explaining an effect of the invention.

As described above, because the correction voltage varies depending on the position in a direction (x-direction) perpendicular to the ion-traveling direction and the asymmetric voltage, it is possible to obtain information of spectra corresponding to different correction voltages simultaneously by aligning the detectors in the x-direction. It is also possible to determine the positions of the detectors on the x-axis based on the values of the calibration voltages on the x-axis. The detectors are sometimes disposed at a regular interval or may be disposed at irregular intervals to achieve desired calibration voltages. FIG. 4 is a diagram explaining the usefulness of this system. This is an example of the detection at the cation detection electrode 3 (about 39 channels) when SV=2.1 kV, Va=−3 V and Vb=3 V were applied. As the samples, 2-(2-methoxyphenyl)-N-methylethanamine molecule ions and 3,4-methylenedioxyphenethylamine molecule ions, which have similar mass numbers and similar molecular structures, were measured. At around CV=0.2 V, only 2-(2-methoxyphenyl)-N-methylethanamine molecule ions are strongly detected; while at around CV=1.1 V, only 3,4-methylenedioxyphenethylamine molecule ions are strongly detected. In the conventional examples, the correction voltages are scanned temporally from −3 V to 3 V and thus it takes time to obtain similar data. However, by using this technique, transmittance data corresponding to different correction voltages can be detected simultaneously and thus the speed has become 10 times or more faster. In addition, it can be seen that spectra can be obtained without deteriorating the resolution, unlike the case in which different DC voltages are applied to electrodes sectioned as in PTL 1.

When the charge-up phenomenon is caused by the collision of ions with insulators, the transmittance of ions decreases and the ion resolution deteriorates. However, by disposing electrodes such as electrodes 14 and electrodes 15 near the paths of the ions on the substrate 12 and the substrate 13, the charge-up phenomenon can be prevented. By using a region formed by a direct-current electric field at the inlet edge of the separation electrode 1 to which the RF voltage is applied, like the electrodes 15, it is possible to decrease the degree of the phenomenon in which ions are deflected by the fringing electric field at the edge of the separation electrode 1 and the transmittance is reduced.

Example 2

Figure 5:
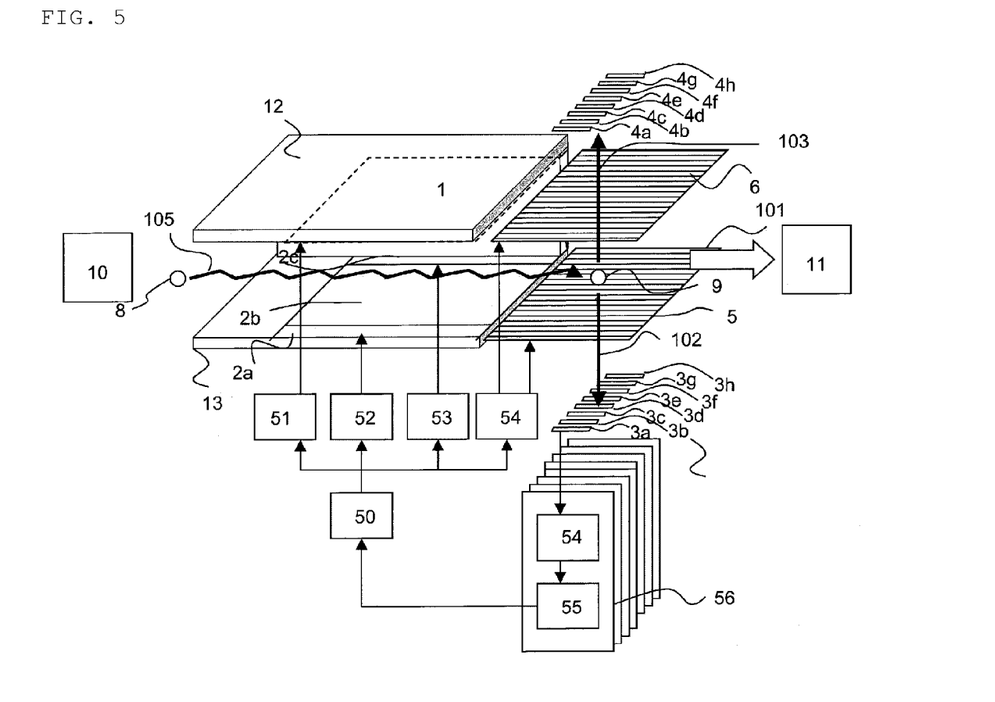
FIG. 5 A diagram showing another example of the constitution of the invention.

FIG. 5 is a constitution diagram of the ion mobility separation device of the second Example to which this system is applied. The constitution is the same as that of Example 1 until the ions from the ion source pass through the separation electrodes 1 and 2; however, in this Example, time-of-flight ion mobility separation has been combined after the ions have passed through the separation electrodes. A direct-current pulse voltage with an interval of several Hz or more and several hundred Hz or less is applied to mesh electrodes 5 and 6. From this, an ion 9 after passing through the separation electrodes 1 and 2 is accelerated in a traveling direction 102 when the ion 9 is a cation, and in a traveling direction 103 when the ion 9 is an anion. An electric field approximately parallel to each traveling direction is formed each between the mesh electrode 5 and the detection electrode 3 and between the mesh electrode 6 and the detection electrode 4. The parallel electric fields can be formed using plate electrodes or materials coated with conductive materials, although they are not shown in the diagram. In the parallel electric fields, ions with larger ion mobilities travel faster. Therefore, by measuring the flight times, ion species can be separated according to their ion mobilities. Moreover, in this Example, conditions with different correction voltages can be set depending on the position in the x-direction, and thus the conditions of the correction voltages and the flight times of ions can be simultaneously obtained.

Figure 6:
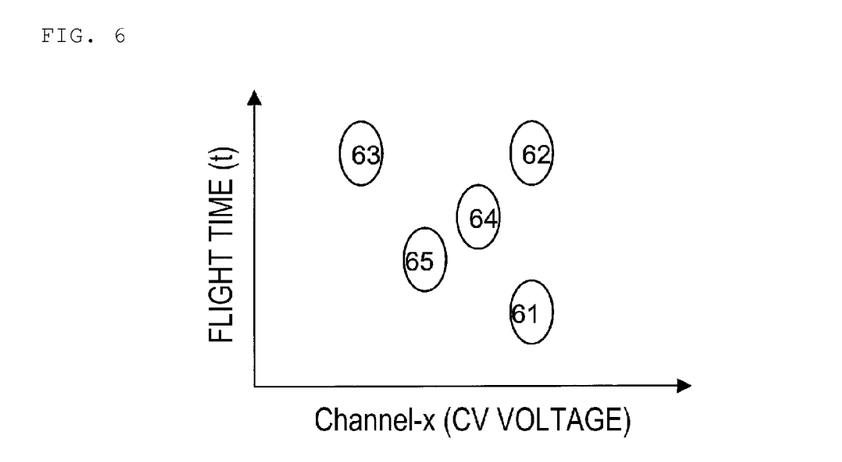
FIG. 6 A diagram explaining an effect of another example of the constitution of the invention.

A diagram explaining an effect of this system is shown in FIG. 6. Shown is an example in which five ion species, A to E, were detected as the samples. Although a signal 61 derived from the ion species A cannot be separated from a signal 62 derived from the ion species B on the x-axis of the detection electrodes (corresponding to the correction voltage), the signal 61 can be separated from the signal 62 by the flight time. On the other hand, although a signal 63 derived from the ion species C cannot be separated from the signal 62 derived from ion species B by the flight time information, the signal 63 can be separated from the signal 62 on the x-axis of the detection electrodes (corresponding to the correction voltage). Thus, by using this Example, measurement with high two-dimensional resolution in a short time is possible.

Example 3

Figure 7:
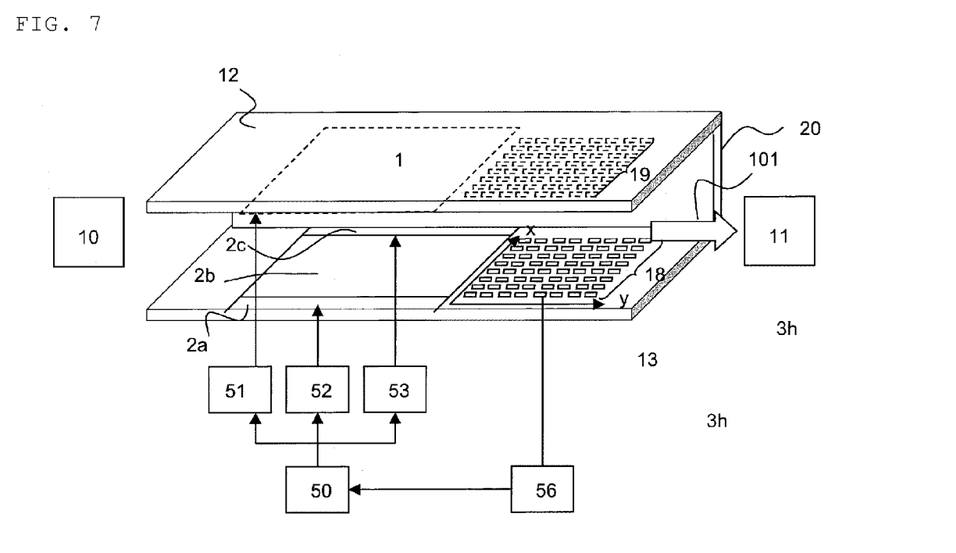
FIG. 7 A diagram showing another example of the constitution of the invention.

FIG. 7 is a constitution diagram of the ion mobility separation device of the third Example to which this system is applied. The constitution is the same as that of Example 1 until the ions from the ion source pass through the separation electrodes 1 and 2; however, in this Example, two-dimensionally arrayed detection electrodes 18 and 19 have been used to detect the ions which have passed through the separation electrodes. A direct-current voltage of about several V is applied to detection electrodes 18 and 19. From this, the ion 9 after passing through the separation electrodes 1 and 2 is accelerated toward detection electrode 18 when the ion 9 is a cation and toward detection electrode 19 when the ion 9 is an anion. Ions with larger ion mobilities reach electrodes closer to the separation electrodes (values on the y-axis of the detection electrodes are smaller). In addition, flight time data of ions with different correction voltages can be obtained by the x-axis of the detection electrodes.

Figure 8:
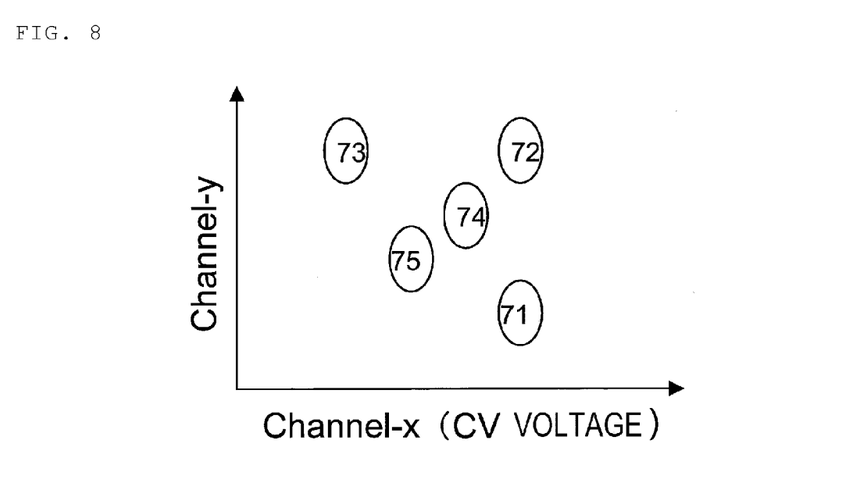
FIG. 8 A diagram explaining an effect of another example of the constitution of the invention.

A diagram explaining an effect of this system is shown in FIG. 8. Shown is an example in which five ion species, A to E, were detected as the samples. Although a signal 71 derived from the ion species A cannot be separated from a signal 72 derived from the ion species B on the x-axis of the detection electrodes (corresponding to the correction voltage), the signal 71 can be separated from the signal 72 on the y-axis of the detection electrodes (corresponding to the ion mobility). On the other hand, although the signal 73 derived from the ion species C cannot be separated from the signal 72 derived from the ion species B on the y-axis of the detection electrodes (corresponding to the ion mobility), the signal 73 can be separated from the signal 72 on the x-axis of the detection electrodes (corresponding to the correction voltage). Thus, by using this Example, measurement with high two-dimensional resolution in a short time is possible.

In this regard, although examples in which an atmospheric-pressure ion source was used as the ion source have been described in the Examples, it is possible to use ions generated at a high pressure or a low pressure and combine them with any of the separation devices of Example 1 to Example 3.

In addition, although examples in which the ion mobility separation systems were placed at atmospheric pressure have been described, the separator device can be placed in a low vacuum to at a high pressure, in which ion mobility separation is considered to be possible.

Furthermore, in the Examples, although examples in which a detector ammeter and a weak-current amplifier were used in combination as the detector have been described, it is possible to combine with semiconductor detectors such as a charge coupled device and a complementary metal oxide semiconductor, and ion detection methods such as an electron multiplier.

REFERENCE SIGNS LIST

1 Separation electrode (conductive electrode), 2 separation electrode, 3 detection electrode (for cations), 4 detection electrode (for anions), 5 mesh electrode, 6 mesh electrode, 8 ion, 9 ion, 10 ion source, 11 pump, 12 substrate, 13 substrate, 14 electrode, 15 electrode, 18 detection electrode (for cations), 19 detection electrode (for anions), 20 spacer, 50 controller, 51 power source, 52 power source, 53 power source, 54 amplifier, 55 data recorder, 56 signal processor, 57 pulse acceleration power source, 61 signal derived from sample A, 62 signal derived from sample B, 63 signal derived from sample C, 64 signal derived from sample D, 65 signal derived from sample E, 71 signal derived from sample A, 72 signal derived from sample B, 73 signal derived from sample C, 74 signal derived from sample D, 75 signal derived from sample E, 101 gas-flow direction, 102 ion-traveling direction, 103 ion-traveling direction, and 105 ion-traveling direction.

The invention claimed is:
1. An ion mobility separation device comprising:
an ion source generating ions;
a pair of spaced plate electrodes defining a flow path between a sample inlet and a sample outlet of the ions;

a voltage controller applying an asymmetric time-varying voltage and direct-current voltages to the plate electrodes; and current detectors aligned in a direction perpendicular to a flow-path direction and a direction in which the asymmetric time-varying voltage is applied:

wherein at least one of the pair of plate electrodes contains a first electrode section having a first conductivity, a second electrode section having a second conductivity, and a third electrode section interposed between the first electrode section and the second electrode section, wherein the third electrode section has a third conductivity smaller than the first conductivity and the second conductivity;

the first electrode section, the third electrode section and the second electrode section are aligned in a direction perpendicular to the flow-path direction and the direction in which the asymmetric time-varying voltage is applied; and the voltage controller applies different direct-current voltages to the first electrode section and the second electrode section.

2. The ion mobility separation device of claim 1, wherein the first electrode section or the second electrode section contains a metal, and the third electrode section contains any one of a metal oxide thin film, a metal nitride thin film and an organic conductor.

3. The ion mobility separation device of claim 1, wherein the third electrode section has an end-to-end resistance value of 50 Ω or more and 5 kΩ or less.

4. The ion mobility separation device of claim 1, which further comprises an electrode surrounding the lateral sides of the sectioned current detectors and the sample-outlet side of the current detectors.

5. The ion mobility separation device of claim 1, which further comprises a pair of electrodes sandwiching the plate electrodes and the sample outlet, wherein a voltage is applied to the pair of electrodes by the voltage controller:

wherein the current detectors sandwich the pair of electrodes; and the voltage controller continuously accelerates the ions passed through the plate electrodes in a direction perpendicular to the flow-path direction by applying the voltage to the pair of electrodes.

6. The ion mobility separation device of claim 1, wherein lines of the current detectors are aligned in the flow-path direction.

\* \* \* \* \*